United States Patent
Xu et al.

(10) Patent No.: US 10,952,984 B2
(45) Date of Patent: Mar. 23, 2021

(54) ALL-TRANS RETINOIC ACID INJECTANT AND APPLICATION

(71) Applicant: HIGHFIELD BIOPHARMACEUTICAL CORPORATION, Hangzhou (CN)

(72) Inventors: Yuhong Xu, Hangzhou (CN); Xiaolong Chen, Hangzhou (CN); Anjie Zheng, Hangzhou (CN); Lieyi Wu, Hangzhou (CN)

(73) Assignee: HIGHFIELD BIOPHARMACEUTICAL CORPORATION, Hangzhou (CN)

( * ) Notice: Subject to any disclaimer, the term of this patent is extended or adjusted under 35 U.S.C. 154(b) by 0 days.

(21) Appl. No.: 16/326,216

(22) PCT Filed: Aug. 17, 2017

(86) PCT No.: PCT/CN2017/097868
§ 371 (c)(1),
(2) Date: May 9, 2019

(87) PCT Pub. No.: WO2018/033117
PCT Pub. Date: Feb. 22, 2018

(65) Prior Publication Data
US 2019/0282530 A1 Sep. 19, 2019

(30) Foreign Application Priority Data

Aug. 18, 2016 (CN) .................. 2016 1 0681196 4

(51) Int. Cl.
| | | |
|---|---|---|
| *A61K 31/20* | (2006.01) | |
| *A61K 9/127* | (2006.01) | |
| *A61K 9/00* | (2006.01) | |
| *A61K 31/203* | (2006.01) | |
| *A61P 35/00* | (2006.01) | |
| *A61K 9/107* | (2006.01) | |
| *A61K 31/19* | (2006.01) | |
| *A61K 9/08* | (2006.01) | |
| *A61K 9/10* | (2006.01) | |
| *A61K 9/14* | (2006.01) | |

(52) U.S. Cl.
CPC .......... *A61K 31/203* (2013.01); *A61K 9/0019* (2013.01); *A61K 9/08* (2013.01); *A61K 9/10* (2013.01); *A61K 9/107* (2013.01); *A61K 9/14* (2013.01); *A61K 31/19* (2013.01); *A61P 35/00* (2018.01)

(58) Field of Classification Search
CPC .............................. A61K 9/0019; A61K 9/127
USPC ................................. 424/450, 400; 514/559
See application file for complete search history.

(56) References Cited

U.S. PATENT DOCUMENTS 5,811,119 A * 9/1998 Mehta .................... A61K 9/127
424/450

FOREIGN PATENT DOCUMENTS

| CN | 101244039 A | 8/2008 |
|---|---|---|
| EP | 041795 | * 12/1981 |

OTHER PUBLICATIONS

Strickley "Solubilizing Excipients in Oral and injectable formulations," Pharmaceutical Research, 2004, vol. 21, No. 2, pp. 201-230 (Year: 2004).*

(Continued)

*Primary Examiner* — Shengjun Wang
(74) *Attorney, Agent, or Firm* — Global IP Services; Tianhua Gu

(57) ABSTRACT

The present disclosure provides an all-trans retinoic acid injectable formulation and its application for a preparation of a pharmaceutical product for treating tumor. The all-trans retinoic acid injectable formulation includes all-trans retinoic acid and solubilizers. The apparent solubility of the all-trans retinoic acid is increased from 0.01 mg/mL to 0.1 mg/mL or more. The injectable formulation can reduce the activity of an infiltrated immuno-suppressive cell population within blood or tumor tissue of a cancer patient, and improve immune clearing effects against tumors. It can be applied independently or together with other pharmaceutical products to inhibit tumor growth and prevent tumor recurrence.

9 Claims, 9 Drawing Sheets

(56) References Cited

OTHER PUBLICATIONS

Hu et al. "Pharmacokinetics and antitumor efficacy of DSPE-PEG2000 polymeric liposomes loaded with quercetin and temozolomide: analysis of their effectiveness in enhancing the chemosensitization of drug-resistant glioma cells," International J, Molecular Medicine, Jan. 2016, vol. 37, pp. 690-702 (Year: 2016).*

Karmakar et al. "Combination of all-trans retinoic acid and paclitaxel-induced differentiation and apoptosis in human glioblastoma U87MG xenografts in nude mice," Cancer, 2008, vol. 112, No. 3, pp. 596-607 (Year: 2008).*

杨静雯, 全反式维甲酸脂质体 小鼠体内的药动学 与组织分布学. 沈阳药科大学学报. Dec. 31, 2007 (Dec. 31, 2007), ISSN: 1006-2858, pp. 731-735, particularly p. 731, left-hand column, paragraph 1, right-hand column, sections 2.1 and 2.2 and p. 732, section 2.4, (Yang, Jingwen et al., Pharmacokinetics and Tissue Distribution Study of ATRA Liposome in Mice, Journal of Shenyang Pharmaceutical).

胡连栋, 全反式维甲酸固体脂质纳米粒的制备及 其体内外评. 药学学报. Dec. 31, 2005 (Dec. 31, 2005), ISSN: 0513-4870, pp. 71-75, particularly p. 72, left-hand column, paragraph 2, last paragraph to right-hand column, paragraph 1, and p. 73, left-hand column, paragraph 2 and 3, (Hu, Liandong et al., Preparation of Solid Lipid Nanoparticles Loaded with All-Trans Retinoic Acid and their Evaluation in Vitri and in Vivo. Acta Pharmaceutica Sinica).

魏慧芹等, 全反式维甲酸的临床应用及研究进展, 医学综述. Mar. 31, 2014 (Mar. 31, 2014), ISSN: 1006-2084, pp. 1088-1090, particularly p. 1089, section 2. (Wei, Huiqin et al., Clinical Application and Research Progress of All-trans-retinoic Acid, Medical Recapitulate).

* cited by examiner

ALL-TRANS RETINOIC ACID INJECTANT AND APPLICATION

CROSS REFERENCE TO RELATED PATENT APPLICATION

The present application is the US national stage of PCT/CN2017/097868 filed on Aug. 17, 2017, which claims the priority of the Chinese patent application No. CN2016106811964 filed on Aug. 18, 2016, which application is incorporated herein by reference.

BACKGROUND OF THE PRESENT DISCLOSURE

Field of Disclosure

The present disclosure relates to the technical field of biopharmaceuticals, and in particular to an all-trans retinoic acid injectable formulation and its application.

Description of Related Arts

Retinoic acid is a vitamin A metabolite in the body. As a drug, all-trans retinoic acid (ATRA) is mostly used to treat acne. It is also an important drug for the treatment of acute promyelocytic leukemia (APL). Currently, all-trans retinoic acid is clinically administered in oral dosage forms.

All-trans retinoic acid (ATRA) affects gene expression by binding to specific receptors (RARs, RXRs and RORs) in cells. In the treatment of acute promyelocytic leukemia, it can promote the differentiation of APL cells and the degradation of PML/RARa gene to achieve therapeutic effects (Effectiveness and Pharmacokinetics of Low-Dose All-trans Retinoic Acid (25 mg/m$^2$) in Acute Promyelocytic Leukemia. Blood 82, 12, 1993. P. 3560). There are also literatures suggesting that ATRA can promote the differentiation of myeloid-derived suppressor cells (MDSCs) in cancer patients and modulate myeloid-derived cells in tumor tissues (All-trans-Retinoic Acid Improves Differentiation of Myeloid Cells and Immune Response in Cancer Patients. Cancer Res 2006; 66: (18). Sep. 15, 2006). MDSCs were first discovered in the 1980s and were found to consist of relatively immature cells at different degrees of differentiation. A large number of myeloid-derived cells labeled positive for CD11b and Gr-1 were found in the bone marrow, blood, lymphoid organs and tumor infiltrating sites of tumor-bearing mice. These cells are CD34$^+$CD33$^+$CD13$^+$ in human body and can form clones on agar like myeloid-derived precursor cells. In the tumor microenvironment, myeloid-derived suppressor cells down-regulate the killing activity of effector T cells and inhibit the maturation of DC cells by secreting arginase, ROS and IL-6. In addition, ATRA was reported to have an effect of promoting the differentiation of cancer stem cells (Targeting cancer stem cells in glioblastoma multiforme using mTOR inhibitors and the differentiating agent all-trans retinoic acid. ONCOLOGY REPORTS 30: 1645-1650, 2013).

However, the clinical application of the all-trans retinoic acid drug is limited due to the following obstacles: 1) the all-trans retinoic acid has very low water solubility (4.77e-03 g/L); and 2) the all-trans retinoic acid has a short plasma half-life, but the drug efficacy requires maintaining a certain blood concentration over a longer period of time and especially in the target organ. At present, only oral dosage forms are available and used in clinical studies and the bioavailability is only 30% or lower. However, many studies showed that ATRA has the ability to induce differentiation only at a certain blood concentration or above. Therefore, it is particularly important to find an injectable formulation with higher apparent concentrations of all-trans retinoic acid.

SUMMARY OF THE PRESENT DISCLOSURE

In order to overcome the problems in the prior art, the present disclosure has an objective to provide an all-trans retinoic acid injectable formulation and its application.

In order to achieve the above and other related objectives, the present disclosure adopts the following technical solutions:

In a first aspect of the present disclosure, an all-trans retinoic acid injectable formulation is provided, the all-trans retinoic acid injectable formulation comprises all-trans retinoic acid and solubilizers.

Preferably, the solubilizer is selected from any one or a combination of more of lipid, Cremophor EL, PVP, HPMC, Pluronic block copolymer, cyclodextrin or PEG.

Preferably, the mass ratio of the solubilizer to the all-trans retinoic acid is (10-80):1.

Preferably, the lipid is selected from any one or a combination of more of phospholipid, cholesterol or pegylated phospholipid.

Preferably, the mass ratio of the lipid to the all-trans retinoic acid is (20-80):1.

Preferably, the phospholipid is selected from PC phospholipid. Further preferably, the phospholipid is selected from any one or a combination of more of EPC, HSPC or DPPC.

Preferably, the molecular weight of the pegylated phospholipid is in the range of 50-10000.

Preferably, the all-trans retinoic acid injectable formulation is a solution, a suspension, an emulsion, or a sterile powder for injection.

Further preferably, when the all-trans retinoic acid injectable formulation is a solution, a suspension, or an emulsion, the all-trans retinoic acid injectable formulation contains a solvent, and the solvent contains an isosmotic adjusting agent.

Preferably, the isosmotic adjusting agent is sodium chloride. The mass percent by volume of the sodium chloride in the solvent is 0.5-0.9%.

Preferably, the injectable formulation further contains a protective agent. The protective agent is sucrose. The mass percent by volume of the sucrose in the solvent is 2-5%.

The mass percent by volume refers to the mass g of solute contained per 100 mL of solvent.

Preferably, in the all-trans retinoic acid injectable formulation the concentration of the all-trans retinoic acid is greater than or equal to 0.1 mg/mL. Further preferably, in the all-trans retinoic acid injectable formulation, the concentration of the all-trans retinoic acid is greater than or equal to 1.0 mg/mL. More preferably, in the all-trans retinoic acid injectable formulation, the concentration of the all-trans retinoic acid is in the range of 1-5 mg/mL.

Further preferably, the administration route of the injectable formulation is selected from intradermal injection, subcutaneous injection, intramuscular injection, and intravenous injection.

In a second aspect of the present disclosure, an application of the aforementioned all-trans retinoic acid injectable formulation for the preparation of a pharmaceutical product for treating a tumor is provided.

Preferably, the pharmaceutical product for treating a tumor is a drug for abnormal myeloid-derived suppressor cells, induction of differentiation of myeloid-derived suppressor cells, and inhibition of tumor proliferation and recurrence in cancer patients.

Further preferably, the myeloid-derived suppressor cells are myeloid-derived suppressor cells of breast cancer, colon cancer, ovarian cancer, lung cancer, kidney cancer, stomach cancer, liver cancer, cervical cancer, endometrial cancer, bladder cancer, prostate cancer, pancreatic cancer, colorectal cancer, basal cell carcinoma, melanoma, follicular lymphoma or small lymphocytoma.

In a third aspect of the present disclosure, application of the aforementioned all-trans retinoic acid injectable formulation for the preparation of a pharmaceutical product is provided, the pharmaceutical product has any one or more of the following effects:

(1) decreasing the number of myeloid-derived suppressor cells (MDSCs) in tumor infiltrating cells;

(2) inducing differentiation of tumor infiltrating $CD33^+$ $HLA-DR^-$ cells;

(3) promoting phenotypic changes of $CD33^+$ cells in peripheral blood mononuclear cells (PBMCs) of cancer patients;

(4) decreasing inhibition of T cells by $CD33^+HLA-DR^-$ cells in peripheral blood mononuclear cells (PBMCs);

(5) inducing apoptosis of tumor cells;

(6) increasing the proportion of infiltrating lymphocytes in tumor tissues;

(7) inhibiting tumor cell metastasis; and (8) delaying tumor growth.

In a fourth aspect of the present disclosure, a method for treating a tumor is provided, comprising administering the all-trans retinoic acid injectable formulation as described above to a patient. The particular dosage administered is within the purview well known to those skilled in the art.

Compared with the prior art, the present disclosure has the following beneficial effects:

(1) It has been found and proved through long-term experiments that the all-trans retinoic acid injectable formulation prepared by the present disclosure increases the solubility of the all-trans retinoic acid from 0.01 mg/mL in the prior art to at least 0.1 mg/mL or more, which is at least 10 times higher.

(2) The application of the injectable formulation can effectively regulate the microenvironment of tumor development and can effectively induce differentiation of tumor-associated macrophages. The plasma terminal half-life of the present disclosure can be as long as 8-12 hours when administered by intravenous injection or intravenous drip. After treatment by the present disclosure, differentiation or apoptosis of 40%-70% of myeloid-derived suppressor cells in tumors can be promoted, and formation of mature dendritic cells (DCs) can be induced. The level of interleukin-6 (IL-6) secreted by myeloid-derived suppressor cells is significantly decreased after treatment by the preparation. The injectable formulation has an immunotherapy effect when applied independently or together with another pharmaceutical product, can be used to inhibit tumor cell proliferation and tumor recurrence, and thus having the great medical utility.

DETAILED DESCRIPTION OF THE PREFERRED EMBODIMENTS

All-Trans Retinoic Acid Injectable Formulation

Figure 1:
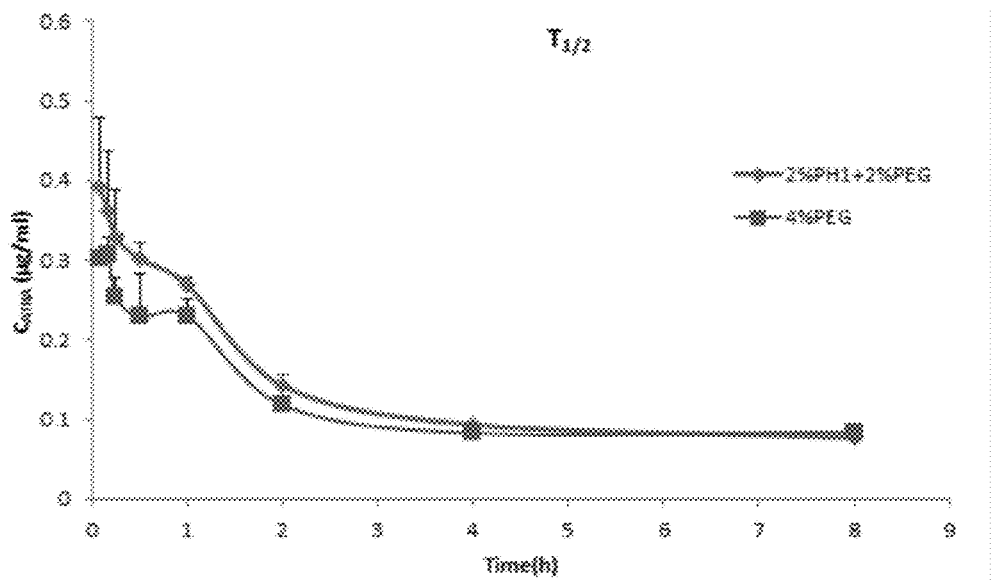
FIG. 1: Blood concentration curves of EPC liposome formulations in mice.

The all-trans retinoic acid injectable formulation of the present disclosure comprises all-trans retinoic acid and a solubilizer.

The solubilizer is selected from any one or a combination of more of lipid, Cremophor EL, PVP, HPMC, Pluronic block copolymer, cyclodextrin or PEG.

The mass ratio of the solubilizer to the all-trans retinoic acid is (10-80):1.

The lipid is selected from any one or a combination of more of phospholipid, cholesterol or pegylated phospholipid.

The mass ratio of the lipid to the all-trans retinoic acid is (20-80):1. The mass ratio of the lipid to the all-trans retinoic acid can also be (20-50):1.

The phospholipid can be selected from PC phospholipid. Further, the phospholipid is selected from any one or a combination of more of EPC, HSPC or DPPC.

The molecular weight of the pegylated phospholipid is in the range of 50-10000.

In an embodiment of the present disclosure, the molecular weight of the pegylated phospholipid is 2000.

In an embodiment of the present disclosure, the Cremophor EL is Cremophor RH40.

The all-trans retinoic acid injectable formulation is a solution, a suspension, an emulsion, or a sterile powder for injection.

Further, when the all-trans retinoic acid injectable formulation is a solution, a suspension or an emulsion, the all-trans retinoic acid injectable formulation contains a solvent, and the solvent contains an isosmotic adjusting agent.

The isosmotic adjusting agent may be selected from sodium chloride. The mass percent by volume of the sodium chloride in the solvent is 0.5-0.9%.

The solvent may also contain a protective agent. The protective agent is sucrose. The mass percent by volume of the sucrose in the solvent is 2-5%.

The mass percent by volume refers to the mass (g) of solute contained per 100 mL of solvent.

In the all-trans retinoic acid injectable formulation, the concentration of the all-trans retinoic acid is greater than or equal to 0.1 mg/mL. Further, in the all-trans retinoic acid injectable formulation, the concentration of the all-trans retinoic acid is greater than or equal to 1.0 mg/mL. Furthermore, in the all-trans retinoic acid injectable formulation, the concentration of the all-trans retinoic acid is in the range of 1-5 mg/mL.

Further, the administration route of the injectable formulation is selected from intradermal injection, subcutaneous injection, intramuscular injection, and intravenous injection.

Application of All-Trans Retinoic Acid Injectable Formulation

In the present disclosure, the application may be: application of the all-trans retinoic acid injectable formulation for the preparation of a pharmaceutical product for treating a tumor.

The pharmaceutical product for treating a tumor is a drug for abnormal myeloid-derived suppressor cells, induction of differentiation of myeloid-derived suppressor cells, and inhibition of tumor proliferation and recurrence in cancer patients.

Further preferably, the myeloid-derived suppressor cells are myeloid-derived suppressor cells of breast cancer, colon cancer, ovarian cancer, lung cancer, kidney cancer, stomach cancer, liver cancer, cervical cancer, endometrial cancer, bladder cancer, prostate cancer, pancreatic cancer, colorectal cancer, basal cell carcinoma, melanoma, follicular lymphoma or small lymphocytoma.

The application may also be applied for the preparation of a pharmaceutical product, the pharmaceutical product has any one or more of the following effects:

(1) decreasing the number of myeloid-derived suppressor cells (MDSCs) in tumor infiltrating cells;

(2) inducing differentiation of tumor infiltrating $CD33^+$ $HLA-DR^-$ cells;

(3) promoting phenotypic changes of $CD33^+$ cells in peripheral blood mononuclear cells (PBMCs) of cancer patients;

(4) decreasing the inhibition of T cells by $CD33^+HLA-DR^-$ cells in peripheral blood mononuclear cells (PBMC);

(5) inducing apoptosis of tumor cells;

(6) increasing the proportion of infiltrating lymphocytes in tumor tissues;

(7) inhibiting tumor cell metastasis; and (8) delaying tumor growth.

Method for Treating Tumor

The method for treating a tumor consistent with the present disclosure comprises the step of administering the aforementioned all-trans retinoic acid injectable formulation to a patient. The particular dosage administered is within the purview well known to those skilled in the art.

Before further describing the specific embodiments of the present disclosure, it shall be understood that the protection scope of the present disclosure is not limited to the specific embodiments described below; it also shall be understood that the terminology used in the embodiments of the present disclosure is intended to describe the specific embodiments, and not to limit the protection scope of the present disclosure. The test methods which do not specify the specific conditions in the following embodiments are usually carried out according to conventional conditions or according to the conditions recommended by each manufacturer.

When the embodiments give a numerical range, it shall be understood that, unless otherwise specified in the present disclosure, two endpoints of each numerical range and any one value between the two endpoints may be optional. Unless otherwise defined, all technical and scientific terms used in the present disclosure have the same meaning as commonly understood by those skilled in the art. In addition to the specific methods, equipment, and materials used in the embodiments, according to mastery of the prior art by those skilled in the art and the description of the present disclosure, the present disclosure can also be implemented using any of the methods, equipment, and materials of the prior art that are similar or equivalent to the methods, equipment, and materials described in the embodiments of the present disclosure.

Unless otherwise stated, the experimental methods, detection methods, and preparation methods disclosed in the present disclosure employ conventional techniques in molecular biology, biochemistry, analytical chemistry, cell culture and recombinant DNA in the technical field, and conventional techniques in related fields. These techniques have been well described in the existing literatures, for details, see Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS INENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolfe, eds.), Academic Press, San Diego, 1999; and METHODS IN MOLECULAR BIOLOGY, Vol. 119, Chromatin Protocols (P. B. Becker, ed.) Humana Press, Totowa, 1999 et al.

Embodiment 1

In this embodiment, the following three methods are used to investigate the saturated solubility after solubilization of ATRA by different solubilizers.

(1) Emulsification method: Appropriate amounts of a solubilizer are dissolved in 1 mL of ultrapure water as an aqueous phase; 1 mg of drug is dissolved in 1 mL of organic solvent as an organic phase; the organic phase is added to the aqueous phase during stirring; after stirring overnight the organic solvent is removed by volatilization or rotary evaporation to obtain the drug-containing solution.

(2) Dialysis method: The drug is dissolved in an organic solvent together with a solubilizer, then the solution is mixed with 1 mL of ultrapure water. And the mixed solution is dialyzed in pure water to obtain the drug-containing solution.

(3) Freeze-drying method: Appropriate amounts of a solubilizer are dissolved in 1 mL of pure water, then appropriate amounts of a freeze-drying protective agent are added as an aqueous phase. The drug is dissolved in an organic solvent (tert-butanol, TBA) as an organic phase. The organic phase and the aqueous phase are mixed together at a certain ratio, then the solution is freeze-dried in a freeze drier for 24 hours. Redissolving is carried out by adding 1 mL of ultrapure water in lyophilizate to obtain the drug-containing solution.

Screening is carried out to select the following injectable formulation containing the following solubilizers:

20% Cremophor RH40 and 5% mannitol are dissolved in 1 mL of pure water as an aqueous phase. 3 mg of drug ATRA is dissolved in 1.5 mL of tert-butanol as an organic phase. The organic phase and the aqueous phase are uniformly mixed, then the mixture is loaded into a 5 mL vial and freeze-dried in a freeze drier. The vial is taken out after 24 hours, and a cover is mounted. Before administration, the lyophilizate is redissolved by adding 1 mL of water to obtain the drug suspension. The saturated solubility of the all-trans retinoic acid therein is determined to be 0.1 mg/mL. The average diameter of particles in the suspension is 274 nm±42 nm by a dynamic laser scattering method and can keep stability at room temperature for 10 hours. These results prove the particles have good stability and dispersibility.

Embodiment 2

EPC, HSPC and DPPC are respectively selected as the main lipid materials and mixed with cholesterol and DSPE-PEG2000 according to the molar ratio of PC:Chol:DSPE-PEG2000=2:1:0.125. Then ATRA is added according to the mass ratio of lipid/ATRA respectively 20:1, 40:1, 50:1. In hydration method 5-7 small glass beads are added and rotating hydration is carried out for 30 minutes. The obtained crude sample is extruded by passing through 400 nm, 200 nm, and 100 nm polycarbonate membranes sequentially for 15 times. The average particle diameter of the obtained all-trans retinoic acid-loaded liposomes is in a range of 100 nm±30 nm, with PDI of about 0.1. Free all-trans retinoic acid (ATRA) is removed by a sephadex G-50 microcolumn. In the linear range of a standard curve of the all-trans retinoic acid, the encapsulation efficiency of the amount of ATRA incorporated into the liposome is calculated by acquiring the ratio of the drug ultraviolet absorption peak area value between encapsulated ATRA fractions and total ATRA fractions. The encapsulation efficiencies of the three liposome formulations show that the EPC liposome is 94%, the HSPC liposome is 91% and the DPPC liposome is 76%. The concentrations of ATRA in the three liposome formulations are all 0.3 mg/mL or above.

The all-trans retinoic acid liposomes prepared above are administered by intravenous injection, and the half-life of the ATRA in mice is between 4-12 hours. The plasma-drug concentration curve of the EPC liposome in mice is shown by the red curve in FIG. 1, and the calculated half-life is 247 minutes.

Embodiment 3

0.097 g of hydrogenated soybean phosphatidylcholine (HSPC), 0.031 g of pegylated phospholipid 1,2-distearoyl-sn-glycero-3-phosphoethanolamine-polyethylene glycol 2000 (DSPE-PEG2000) and 0.031 g of cholesterol are weighed and dissolved with 1.6 mL of ethanol. The ethanol mixture is completely dissolved by incubating in a water bath of 70° C. Then the solution is added to 6.4 mL of calcium acetate buffer solution (pH 9.0) and incubated in a water bath of 70° C. for 30 minutes. The obtained crude liposome sample is extruded by passing through 400 nm, 200 nm, 100 nm and 50 nm polycarbonate membranes sequentially for 8 times to obtain liposomes having an average particle diameter of about 90 nm.

The liposomes prepared in the previous step are dialyzed through a dialysis membrane with a 10000 MWCO (Molecular Weight Cut off) to replace the aqueous phase with a 10% sucrose solution (pH 6~7). Then 4 mg/mL suspension of all-trans retinoic acid is added and the drug-loading step is incubated for 45 minutes at 60° C. After incubation, the free all-trans retinoic acid not loading into liposomes is removed by the dialysis membrane with a 10000 MWCO and final all-trans retinoic acid liposome injectable formulation is obtained with a concentration of 2.0 mg/mL ATRA.

The plasma terminal half-life of the ATRA in mice can be as long as 8 to 12 hours when administered by intravenous injection or intravenous drip.

Embodiment 4 All-Trans Retinoic Acid Injectable Formulation Induces Tumor Myeloid-Derived Suppressor Cells Differentiation In Vitro 1. Construction of Tumor Model in Balb/C Mice (1) CT-26 cells in logarithmic growth phase are digested with trypsin and collected by centrifuging at 300 g for 5 minutes. After discarding the supernatant, the cells are resuspended in sterile PBS and the concentration is adjusted to $1 \times 10^7$ cells/mL.

(2) Six-week-old Balb/c mice are purchased and hairs around subcutaneous inoculation site are shaved in advanced. Mice are anesthetized by intraperitoneal injection of 200 μL of 4% chloral hydrate and the prepared $5 \times 10^5$ to $1 \times 10^6$ CT-26 cells suspension is subcutaneously injected into the right underarm region. Continue to raise after inoculation.

(3) After 2 to 3 weeks, the long diameter (L) and short diameter (S) of the inoculated tumor are measured using a vernier caliper, and the tumor volume size (V) is calculated by the formula: $V = \frac{1}{2} \times L \times S^2$. The animal experiment can be performed when the tumor volume reaches to about 100 mm$^3$.

2. Characterization and Sorting of Tumor-Associated Lymphocytes MDSCs (1) The mice are sacrificed by cervical dislocation, and the tumor is subcutaneously removed with forceps and scissors. The tumor tissue is cut into small pieces on a 40 μm cell strainer with gentle shearing force which can avoid from damaging the tumor cell. At the same time the tissues are continuously washed with 5% PBS during the cutting process.

(2) All the small pieces of tissues and the PBS solution are centrifuged and the supernatant is discarded. Mince tissues are transferred into a 15 mL centrifuge tube containing 1 mL of tissue digestion medium, and the tube is incubated on a shaker (200 rpm/minute) under 37° C. for 1 hour.

(3) The digested cells suspension is screened again with the 40 μm cell strainer, and the cells are washed with PBS for 2 to 3 times to remove residual tissue digestion medium, cell debris and dead cells. The conditions of centrifugation are set as 1000 rpm for 5 minutes. Finally, the centrifuged cells are resuspended in PBS to obtain tumor single cell suspension.

(4) The sorting buffer is added at a proportion of $10^7$ cells per 90 μL volume, and the CD11b microbeads are added at a proportion of $10^7$ cells per 100 μL volume.

(5) The microbeads and the cells are thoroughly mixed, and incubated at 4° C. for 30 minutes in the dark. After incubation, 90 μL of buffer is added per $10^7$ cells/1 mL to wash cells by centrifugation at 1000 rpm for 5 minutes. Continue to wash for 2 times with the buffer after centrifugation.

(6) Finally, 500 μL of buffer is added to resuspend the microbeads-binding tumor single cell suspension.

(7) An MS column is placed in a matching magnet and fully saturated by rinsing with appropriate amount of buffer.

(8) After rinsing, the tumor single cell suspension is applied onto the MS column, and the MS column is washed with 1 mL buffer to remove the unlabeled cells.

(9) After repeated washing for 3 to 5 times, the MS column is removed, placed on a 15 mL centrifuge tube and added with 1 mL buffer. By firmly pushing a matching instrument of the MS column into the column, CD11b positive cells are collected from column.

(10) Cell counting is carried out on the CD11b positive cell suspension obtained in the previous step and flow cytometry samples are prepared by adjusting the cell concentration to $10^7$/mL.

(11) Flow cytometry samples are divided into a negative sample, a Gr-1 positive sample, a CD11b positive sample and a test sample. No fluorescent antibody is added to the negative sample to set a negative condition. Single fluorescent antibodies are respectively added to the Gr-1 positive sample and the CD11b positive sample for subsequent fluorescence compensation. A test fluorescent antibody is added to the test sample. In each sample group, 2 to 3 tubes are set in parallel runs.

(12) About $10^6$ cells are resuspended using 100 μL of flow cytometry staining buffer in all the flow tubes. No fluorescent antibody is added in the negative sample, fluorescent anti-Gr-1 antibody is added in the Gr-1 positive sample, fluorescent anti-CD11b antibody is added in the CD11b positive sample, and fluorescent anti-Gr-1 and anti-CD11b antibody are both added in the test sample.

(13) Flow cytometry samples are incubated at 4° C. for 30 minutes in the dark. After incubation, in order to wash away unbound antibodies, 1 mL of staining buffer is added to cells. Then the samples are centrifuged. Cells are washed twice with staining buffer before the cells are finally resuspended with 500 μL of staining buffer and proceeded to run samples on the flow cytometer.

3. All-Trans Retinoic Acid Injectable Formulation Induces Differentiation of Lymphocytes in Peripheral Blood and Tumor Sites (1) The all-trans retinoic acid injectable formulation is prepared according to the methods of embodiments 1, 2, and 3.

(2) MDSCs in the tumor tissues are sorted and the cell concentration is adjusted to $10^7$/mL. The collected cells are inoculated into a 24-well plate at a final concentration of $10^6$/pore.

(3) 20 μL of PBS, 20 μL and 50 μL of all-trans retinoic acid injectable formulation are separately added in the 24-well plate containing cells, and the plate is incubated at 37° C. for 24 hours.

(4) After 1 day of incubation, the cells are incubated with Gr-1 and CD11b, CD11c, CD80, CD86 and MHC-II antibodies, and changes of MDSC and DC in the cells are observed by flow cytometry. The isotype control and fluorescence compensation are added during the flow cytometry.

Figure 2:
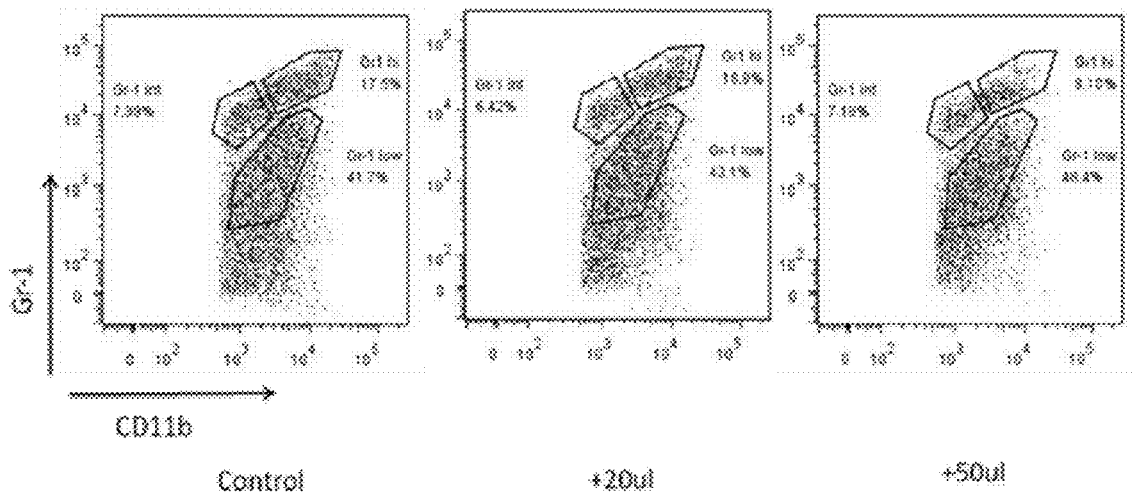
FIG. 2: Inhibition of MDSCs in mouse tumor tissues after treatments using all-trans retinoic acid injectable formulation.

The results of the the all-trans retinoic acid injectable formulation prepared in embodiment 3 are shown in FIG. 2. The results show that the number of Gr-1$^{hi}$ cells decrease significantly by administering different doses of the drug. In the high concentration group the proportion of Gr-1$^{hi}$ cells decreases from 17.5% to 9.10% compared with the control group. However, the proportion of Gr-1$^{int}$ cells does not change much, probably because the cells with high expression of Gr-1 is converted to medium-low expression of Gr-1 under the induction of the all-trans retinoic acid. The proportion of Gr-1$^{low}$ cells increases with the increasing dose of administration, which further indicates that the all-trans retinoic acid induces differentiation of MDSCs and decreases the expression of Gr-1. Since most of the infiltrating MDSCs at the tumor sites are characterized by Gr-1$^{hi}$ or Gr-1$^{int}$, we can conclude that the all-trans retinoic acid injectable formulation can induce differentiation of the MDSCs and decrease its numbers in the tumor sites.

By administration of each of all-trans retinoic acid formulations mentioned in embodiment 1 and embodiment 2, the same experimental results are also observed. Each of the all-trans retinoic acid formulations in embodiment 1 and embodiment 2 can also induce differentiation of the MDSCs and decrease its numbers in the tumor sites.

Embodiment 5 All-Trans Retinoic Acid Injectable Formulation Promotes Immunophenotypic Changes of CD33$^+$ Cells in PBMC from Patients with Head and Neck Mucosal Squamous Cell Carcinoma (HNSCC)

2 mL of peripheral blood is taken from a patient with HNSCC and diluted twice with 2 mL of PBS. The diluted blood is carefully layered on 3 mL of a human lymphocyte separation solution along the inner wall of the test tube. The sample is centrifuged at 300 g for 30 minutes at room temperature (acceleration 2, deceleration 1). The mononuclear cell layer is carefully transferred to a tube and washed twice with 10 mL PBS buffer at 300 g. After the supernatant is discarded, a small amount of PBS is added to obtain a big amount of PBMC, which is maintained at 4° C. for further application. According to the microbeads separation equipment operating manual, myeloid-derived cells in the PBMC are separated by CD33$^+$ microbeads. Cells are cultured in 12-well plate at 5×10$^5$ cells/well with RPMI1640 complete medium (10% FBS added). The all-trans retinoic acid injectable formulation prepared as described in embodiment 1 or embodiment 2 or embodiment 3 is added and the cell plate is cultured for 24 hours. Then the percentage of HLA-DR$^+$ CD11c$^+$ phenotypic DC cells population in myeloid-derived cells is detected by flow cytometry.

Figure 3:
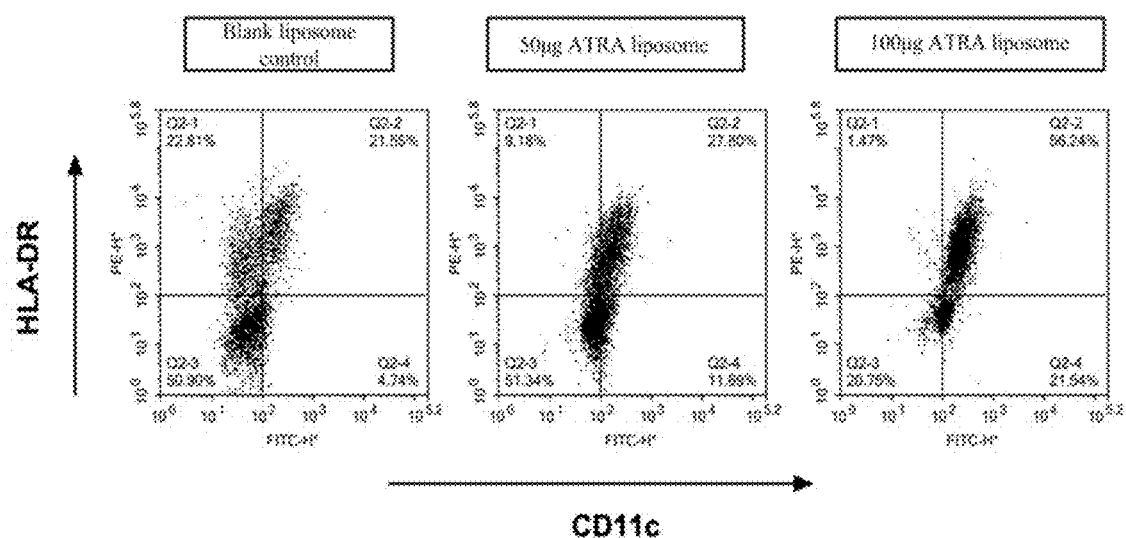
FIG. 3: All-trans retinoic acid injectable formulation promotes differentiation of MDSCs obtained from head and neck mucosal squamous carcinoma patient blood samples.
Figure 4:
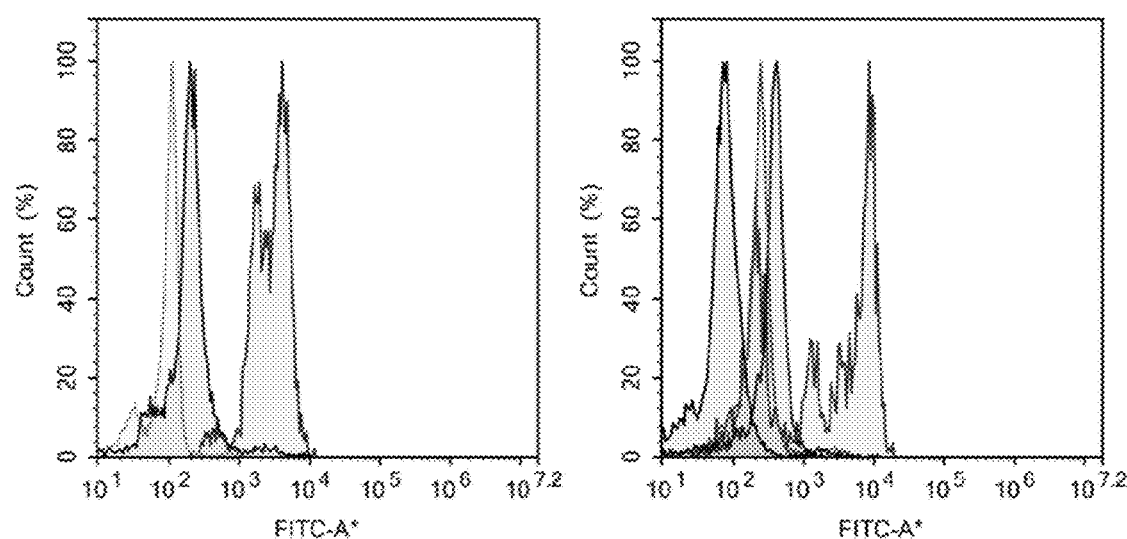
FIG. 4: All-trans retinoic acid injectable formulation significantly reduces iNOS expression in MDSCs in cancer patient samples.

As shown in FIG. 3, flow cytometry results prove that the percentage of the HLA-DR$^+$CD11c$^+$ phenotypic DC cells population in myeloid-derived cells significantly increases with the all-trans retinoic acid injectable formulation prepared in embodiment 3. Furthermore, as shown in FIG. 4, iNOS expression of the cells also significantly decreases. In addition, the expression levels of Arg-1 and IL-6 also significantly decrease.

The same experimental conclusions are also obtained with each of all-trans retinoic acid injectable formulation prepared in embodiments 1 and 2. The percentage of the HLA-DR$^+$CD11c$^+$ phenotypic DC cells population in myeloid-derived cells significantly increases, and the expression levels of Arg-1, iNOS and IL-6 in these cells also significantly decrease using each of the all-trans retinoic acid injectable formulation prepared in embodiments 1 and 2.

Embodiment 6 All-Trans Retinoic Acid Injectable Formulation Significantly Reduces the Number of Cd33$^+$HLA-DR$^-$ MDSCS in Tumor-Infiltrating Myeloid-Derived Cells from Bladder Cancer Patients The clinic tumor sample is obtained from a bladder cancer patient, then rinsed with sterile saline and placed in a RPMI 1640 medium containing penicillin 100 μg/mL, streptomycin 100 μg/mL and 10% fetal bovine serum at 4° C. before laboratory treatment. The tumor tissue is cut into small pieces in medium on ice, then transferred to a 15 mL centrifuge tube containing 2 mL of enzyme digestive fluid (0.6 to 1 mg/mL collagenase I and IV digestive fluid) and gently swirled. The mince tissues mixture is incubated on a shaker (200 rpm/minutes) under 37° C. for 2 hours. The digested single-cells suspension is screened again with the 40 μm cell strainer, and transferred to a 50 ml centrifuge tube, and the cells are slowly washed with sterile PBS. The conditions of centrifugation are set as 300 g for 10 minutes. Finally, the centrifuged cells are resuspended in PBS and counted. According to the microbeads separation equipment operating manual, myeloid-derived cells in the tumor tissue infiltrating cells are separated by $CD33^+$ microbeads. Collected myeloid-derived cells are cultured in 12-well plate at $5\times10^5$ cells/well with RPMI1640 complete medium (10% FBS added). The all-trans retinoic acid injectable formulation prepared as described in embodiment 1 or embodiment 2 or embodiment 3 is added and the cell plate is cultured for 24 hours. Then the percentage of $CD33^+HLA\text{-}DR^-$ MDSCs population in myeloid-derived cells is detected by flow cytometry.

Figure 5:
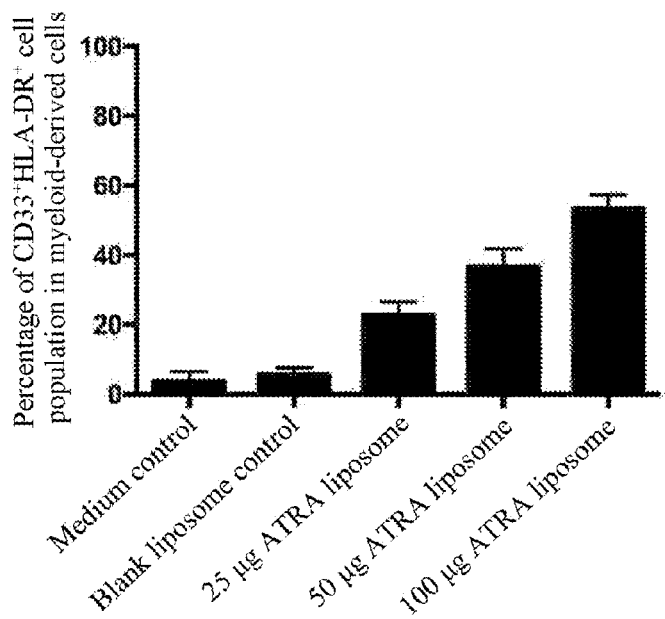
FIG. 5: All-trans retinoic acid injectable formulation acts on tumor tissues in cancer patients, and injectable formulation can significantly reduce MDSCs in the tumor infiltrating myeloid-derived cells of bladder cancer.
Figure 6:
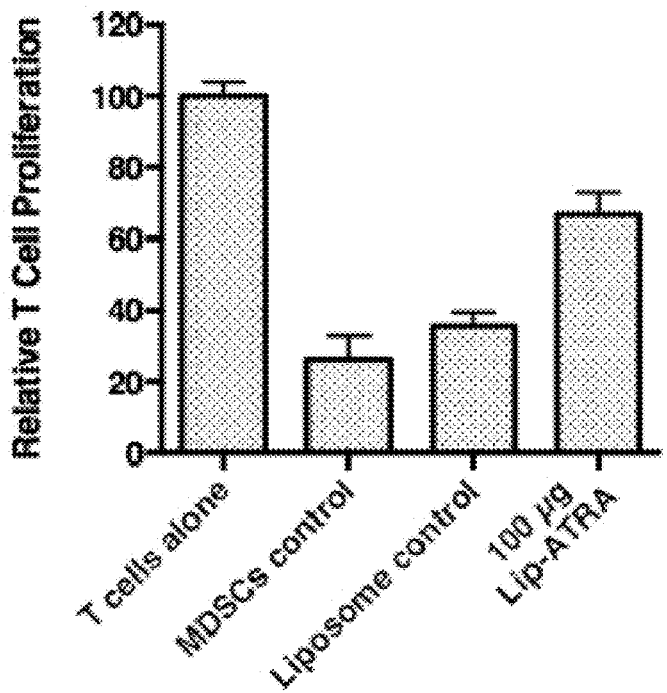
FIG. 6: All-trans retinoic acid injectable formulation can significantly dampen the inhibition of MDSCs on T cells in cancer patients.

As a result, as shown in FIG. 5, the all-trans retinoic acid injectable formulation prepared in embodiment 3 of the present disclosure can significantly reduce the number of $CD33^+HLA\text{-}DR^-$ MDSCs in tumor infiltrating myeloid-derived cells derived from bladder cancer patient. As shown in FIG. 6, the all-trans retinoic acid injectable formulation prepared in embodiment 3 of the present disclosure can reduce the inhibiting effect of MDSCs on T cells.

The same experimental conclusions are also obtained with respect to each of the all-trans retinoic acid injectable formulations prepared in embodiments 1 and 2. Each of all-trans retinoic acid injectable formulations prepared in embodiments 1 and 2 can significantly reduce the number of $CD33^+HLA\text{-}DR^-$ MDSCs in tumor infiltrating myeloid-derived cells derived from bladder cancer patient. Moreover, each of all-trans retinoic acid injectable formulation prepared in embodiments 1 and 2 can reduce the inhibiting effect of MDSCs on T cells.

Embodiment 7 All-Trans Retinoic Acid Injectable Formulation Promotes Apoptosis of Human Breast Cancer Cells MCF-7

A 6-well culture plate is inoculated with $5\times10^5$ MCF-7 cells one day before the experiment, and the cells are cultured overnight at 37° C. in a cell incubator containing 5% $CO_2$. After the culture supernatant is removed from the cell culture plate on the second day, the fresh culture medium and the all-trans retinoic acid injectable formulation prepared in embodiment 1 or embodiment 2 or embodiment 3 are added. The cells are cultured for 24 hours in the 37° C., 5% $CO_2$ cell incubator. After digestion with trypsin without EDTA, cells are collected by centrifugation (300 g) for 5 minutes at 4° C. Then the cells are washed twice with pre-cooled PBS by centrifugation (300 g) for 5 minutes at 4° C. and the number of collected cell is confirmed. The PBS is sucked and discarded. About $15\times10^5$ cells are resuspended with 100 μL of 1× Binding Buffer and then 5 μL of Annexin V-FITC and 10 μL of PI staining solution are added. After incubation in the dark at room temperature for 10~15 minutes, 400 μL of 1× Binding Buffer is added and gently mixed. The samples are kept on ice and detected by flow cytometry within 1 hour.

Figure 7:
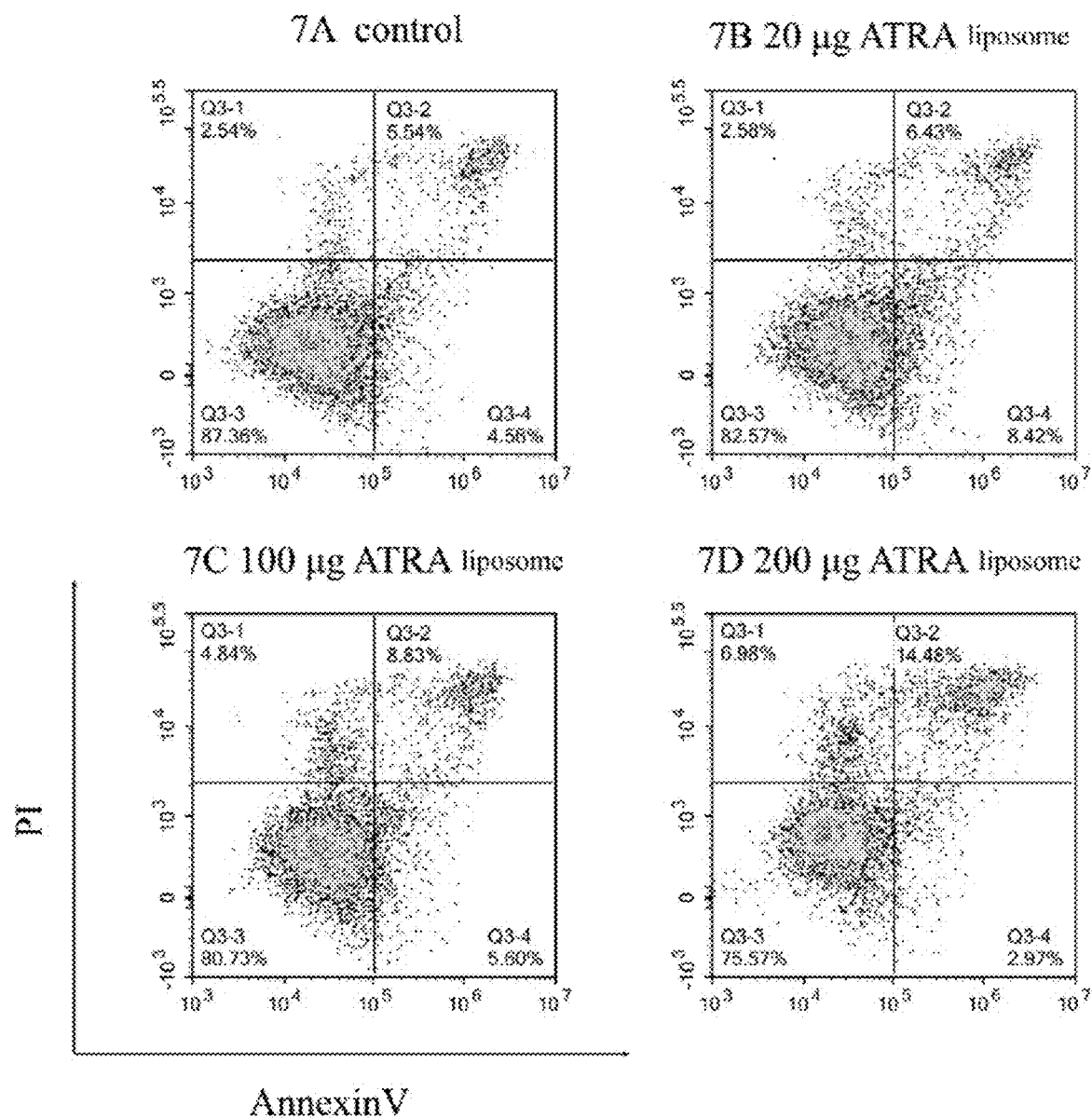
FIG. 7: All-trans retinoic acid injectable formulation promotes apoptosis of human breast cancer cells MCF-7.

As a result, as shown in FIG. 7, the all-trans retinoic acid injectable formulation prepared in embodiment 3 of the present disclosure can significantly promote the apoptosis of the human breast cancer cells MCF-7.

The same experimental conclusions are also obtained with each of the all-trans retinoic acid injectable formulations prepared in embodiments 1 and 2. Each of the all-trans retinoic acid injectable formulations prepared in embodiments 1 and 2 can also significantly promote apoptosis of the human breast cancer cells MCF-7.

Embodiment 8 All-Trans Retinoic Acid Injectable Formulation Promotes Apoptosis of Human Peripheral Blood Leukemia T Cells Jurkat A 6-well culture plate is inoculated with $5\times10^5$ Jurkat cells one day before the experiment, and the cells are cultured overnight at 37° C. in a cell incubator containing 5% $CO_2$. After the culture supernatant is removed from the cell culture plate on the second day, the fresh culture medium and the all-trans retinoic acid injectable formulation prepared in embodiment 1 or embodiment 2 or embodiment 3 are added. The cells are cultured in the incubator for 24 hours under the condition of 37° C. and 5% $CO_2$. The cultured cells are collected by centrifugation (300 g) for 5 minutes at 4° C. and washed twice with pre-cooled PBS by centrifugation (300 g) for 5 minutes at 4° C. The number of collected cell is confirmed. The PBS is sucked and discarded. About $1\sim5\times10^5$ cells are resuspended with 100 μL of 1× Binding Buffer and then 5 μL of Annexin V-FITC and 10 μL of PI staining solution are added. After incubation in the dark at room temperature for 10~15 minutes, 400 μL of 1× Binding Buffer is added and gently mixed. The sample is kept on ice and detected by flow cytometry within 1 hour.

Figure 8:
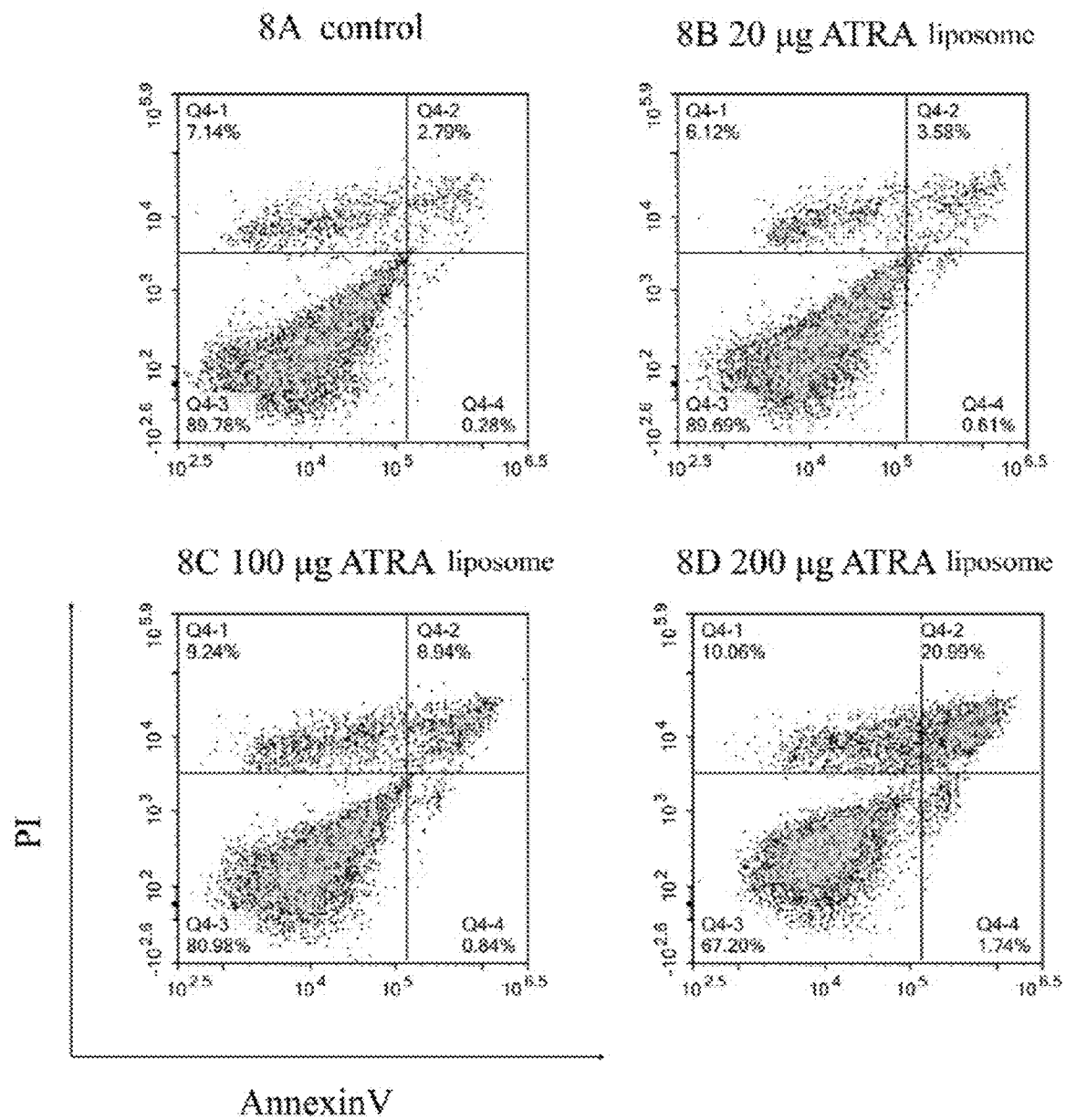
FIG. 8: All-trans retinoic acid injectable formulation promotes apoptosis of human peripheral blood leukemia Jukat cells.

As a result, as shown in FIG. 8, the all-trans retinoic acid injectable formulation prepared in embodiment 3 of the present disclosure can significantly promote the apoptosis of the human peripheral blood leukemia T cells Jurkat.

The same experimental conclusions are also obtained with respect to each of the all-trans retinoic acid injectable formulation prepared in embodiments 1 and 2. Each of the all-trans retinoic acid injectable formulation prepared in embodiments 1 and 2 can significantly promote apoptosis of the human peripheral blood leukemia T cells Jurkat.

Embodiment 9 All-Trans Retinoic Acid Injectable Formulation Inhibits Tumor Growth in Tumor-Bearing Mice The method for establishing a 4T1 subcutaneous xenograft model is described as following: 4T1 tumor cells are incubated in vitro, and a tumor cell suspension is prepared; the prepared tumor cell suspension is evenly blown, a Balb/c mouse (female) is fixed, and the skin of the injection site is sterilized using the ethanol cotton balls. Subcutaneous inoculation is carried out according to 1×106 cells per animal. After injection, the acupuncture site is gently pressed to prevent backflow. The tumor growth is observed after inoculation, the volume of the transplanted tumor is measured, and the longest diameter (a) and the shortest diameter (b) of the tumor are measured with a vernier caliper. The tumor volume (V) is calculated according to $V=\frac{1}{2}\times a\times b\times(a+b)$. The animal experiment can be performed when the tumor volume reaches to about 10 $mm^3$. The all-trans retinoic acid injectable formulation prepared in embodiment 1 or embodiment 2 or embodiment 3 is administrated (5 mg/kg) every other day via intravenous injection.

The control group of mice are injected with the same amount of all-trans retinoic acid-free injectable formulation via intravenous injection and administered (5 mg/kg) every other day. The body weight of the mice is recorded. The average tumor volume is measured and a growth curve is drawn.

Figure 9:
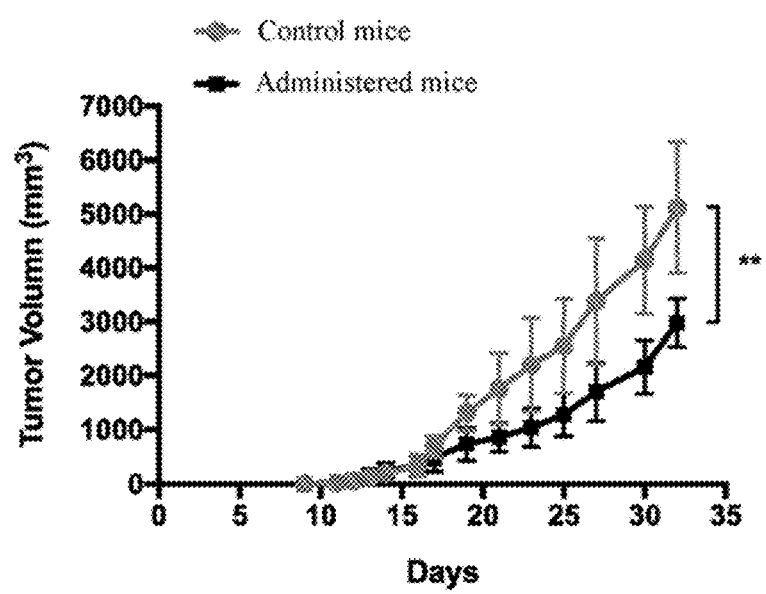
FIG. 9: All-trans retinoic acid injectable formulation promotes tumor size reduction in 4T1 tumor-bearing mice.

As a result, as shown in FIG. 9, the all-trans retinoic acid injectable formulation prepared in embodiment 3 of the present disclosure acts on the 4T1 tumor-bearing mice and reduces the size of mouse tumor tissue volume.

The same experimental conclusions are also obtained with respect to each of the all-trans retinoic acid injectable formulation prepared in embodiments 1 and 2. Each of the all-trans retinoic acid injectable formulation prepared in embodiments 1 and 2 acts on the 4T1 tumor-bearing mice and reduces the size of mouse tumor tissue volume.

Embodiment 10 All-Trans Retinoic Acid Injectable Formulation Significantly Increases the Proportion of Tumor-Infiltrating Lymphocytes in Tumor-Bearing Mouse Model Tumor tissues obtained from the 4T1 tumor-bearing mice of embodiment 9 are fixed in the 4% formaldehyde solution for 3 to 5 days. The fixed tissues are taken out from the fixative solution and trimmed into appropriate size and shape. Tissue blocks are dehydrated with 80%, 90%, 95% and 100% ethanol I, 100% ethanol II and 100% ethanol III. Then after transparent treatment with xylene I and xylene II for 30 minutes each, the tissue blocks are immersed in paraffin I for 1 hour and paraffin II for 6 hours. The tissue blocks are embedded with paraffin by placing the material facing down, and the paraffin blocks are stored at −20° C. when blocks become cool and solidify. The blocks are cut into at 4 μm in thickness, and the sections are placed in water bath at 65° C. for 6 to 12 hours. Finally the sections are mounted onto slides and kept at room temperature.

The immunohistochemical steps are described as following: the slides are deparaffinized and rehydrated, then incubated in 3% $H_2O_2$ for 5 to 10 minutes at room temperature to eliminate the activity of endogenous peroxidase. The slides are rinsed with distilled water and immersed with PBS for 5 minutes. These steps are repeated twice. After that, the slides are blocked with blocking buffer (5 to 10% normal goat serum diluted in PBS) and incubated at room temperature for 10 minutes. The serum is decanted and washing is not carried out. The slides are incubated with primary antibody diluted in recommended antibody diluent at 37° C. for 1 to 2 hours or at 4° C. overnight. Rinse with PBS for 5 minutes each time and the step is repeated for three times. The slides are incubated with secondary antibody diluted in recommended antibody diluent at 37° C. for 10 to 30 minutes. Rinse with PBS for 5 minutes each time and the step is repeated for three times. About 3 to 15 minutes of color development with DAB developer, the slides are fully rinsed with tap water. Then the counterstaining, dehydrating, transparent treatment, and coverslips mounting steps are carried out.

Figure 10:
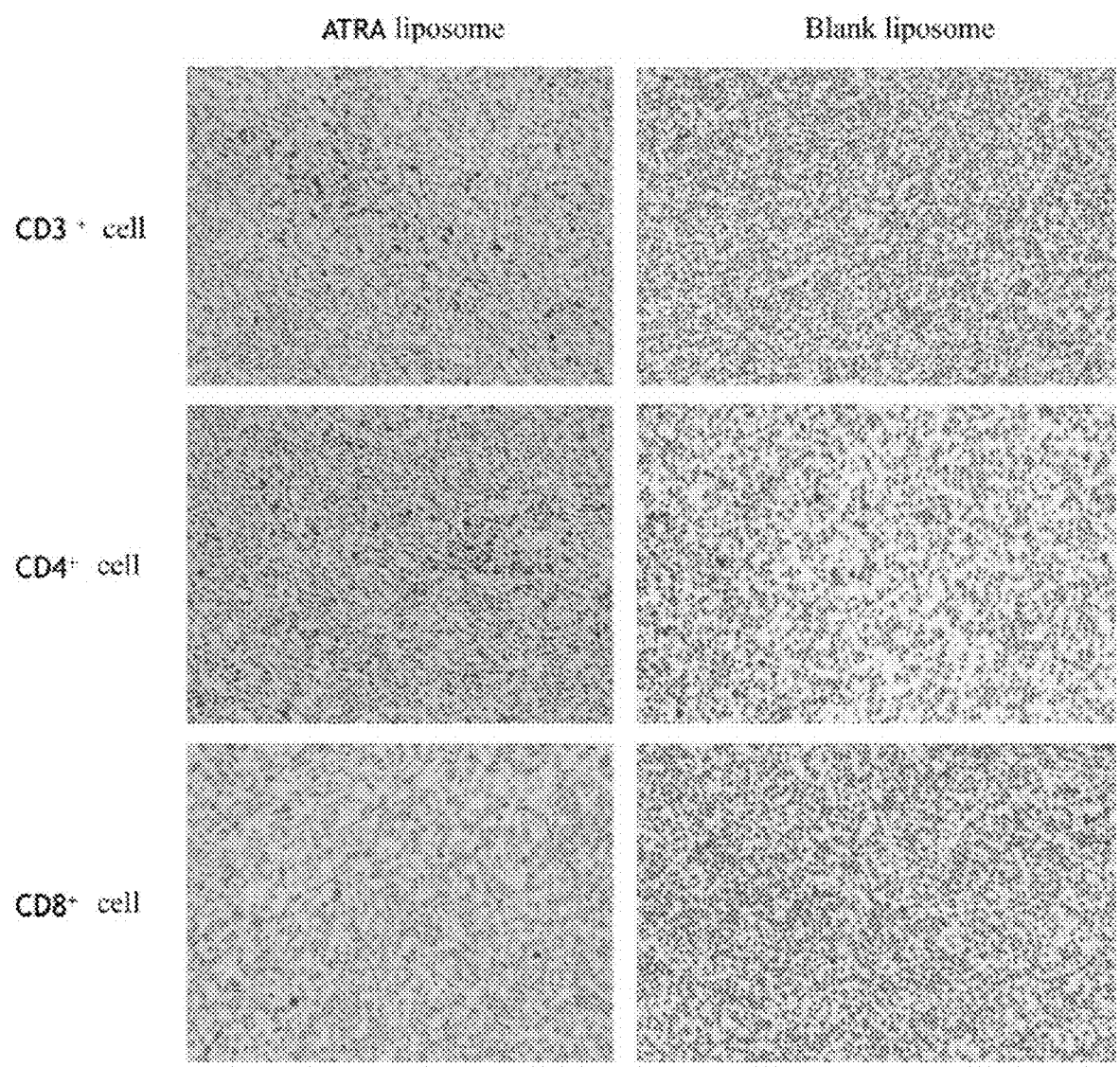
FIG. 10: All-trans retinoic acid injectable formulation increases the number of tumor infiltrating lymphocytes ($CD4^+$ and $CD8^+$ cells).

As a result, as shown in FIG. 10, the all-trans retinoic acid injectable formulation prepared in embodiment 3 of the present disclosure can effectively increase the number of lymphatic infiltrating cells ($CD4^+$ and $CD8^+$ T cells) in tumor-bearing mouse model.

The same experimental conclusions are also obtained with respect to each of the all-trans retinoic acid injectable formulation prepared in embodiments 1 and 2. Each of the all-trans retinoic acid injectable formulation prepared in embodiments 1 and 2 can effectively increase the number of lymphatic infiltrating cells ($CD4^+$ and $CD8^+$ T cells) in tumor-bearing mouse model.

Embodiment 11 All-Trans Retinoic Acid Injectable Formulation Significantly Inhibits Tumor Cell Metastasis in Kidney and Liver of Tumor-Bearing Mouse Model Liver and kidney tissues obtained from the 4T1 tumor-bearing mice of embodiment 9 are fixed in the 4% formaldehyde solution for 3 to 5 days. The fixed tissues are taken out from the fixative solution and trimmed into appropriate size and shape. Tissue blocks are dehydrated with 80%, 90%, 95% and 100% ethanol I, 100% ethanol II and 100% ethanol III. Then after transparent treatment with xylene I and xylene II for 30 minutes each, the tissue blocks are immersed in paraffin I for 1 hour and paraffin II for 6 hours. The tissue blocks are embedded with paraffin by placing the material facing down, and the paraffin blocks are stored at −20° C. when blocks become cool and solidify. The blocks are cut into at 4 μm in thickness, and the sections are placed in water bath at 65° C. for 6 to 12 hours. Finally, the sections are mounted onto slides and kept at room temperature.

The steps for hematoxylin and eosin (H&E) staining of the tissue sections are described as following: firstly, deparaffinating and rehydrating: xylene I for 15 minutes, xylene II for 15 minutes, absolute ethanol I for 5 minutes, absolute ethanol II for 5 minutes, 95% ethanol for 5 minutes, and 80% ethanol for 5 minutes, and immersion cleaning is carried out with tap water for 1 minutes. Staining: the sections are immersed in a hematoxylin staining solution for 5 minutes at room temperature, and the sections are washed with tap water for 1 minute; the sections are immersed in a 1% hydrochloric acid alcohol solution for several seconds, and the sections are washed with tap water until the tissues return to blue; the sections are immersed in eosin stain for 3 to 5 minutes, the sections are washed with tap water to remove the floating color from the sections. Dehydration, transparent treatment, and mounting: the sections are dehydrated with 80% ethanol for 30 seconds, 95% ethanol I for 30 seconds, 95% ethanol II for 30 seconds, absolute ethanol I for 30 seconds and absolute ethanol II for 30 seconds, transparent treatment is carried out with xylene I for 3 minutes and xylene II for 3 minutes, the sections are taken out, mounted with neutral gum and observed for evaluating staining results.

Figure 11:
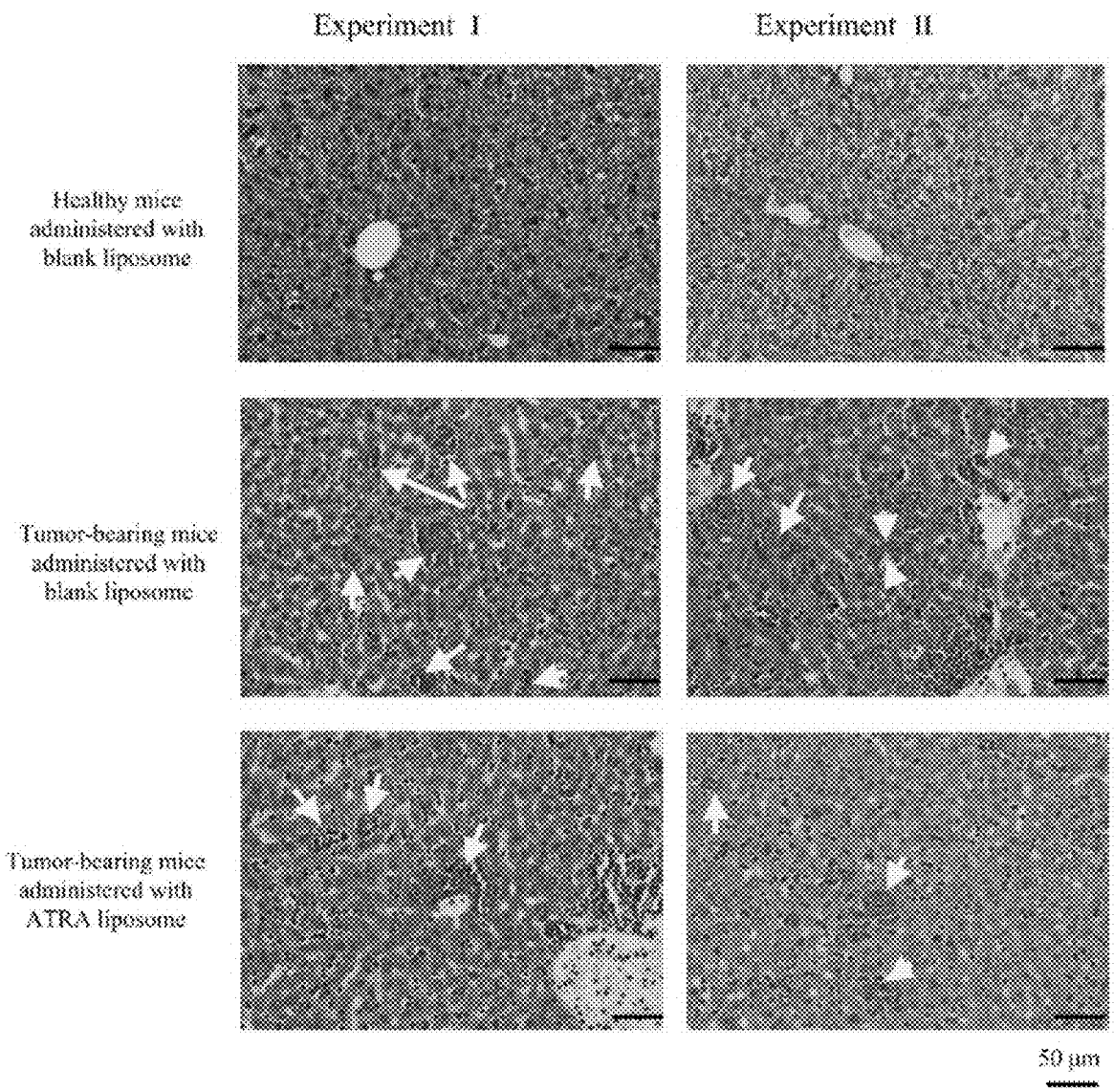
FIG. 11: All-trans retinoic acid injectable formulation reduces liver tissue infiltration and metastasis of tumor cells in 4T1 tumor-bearing mice (white arrows indicate tumor cell invaded lesions).
Figure 12:
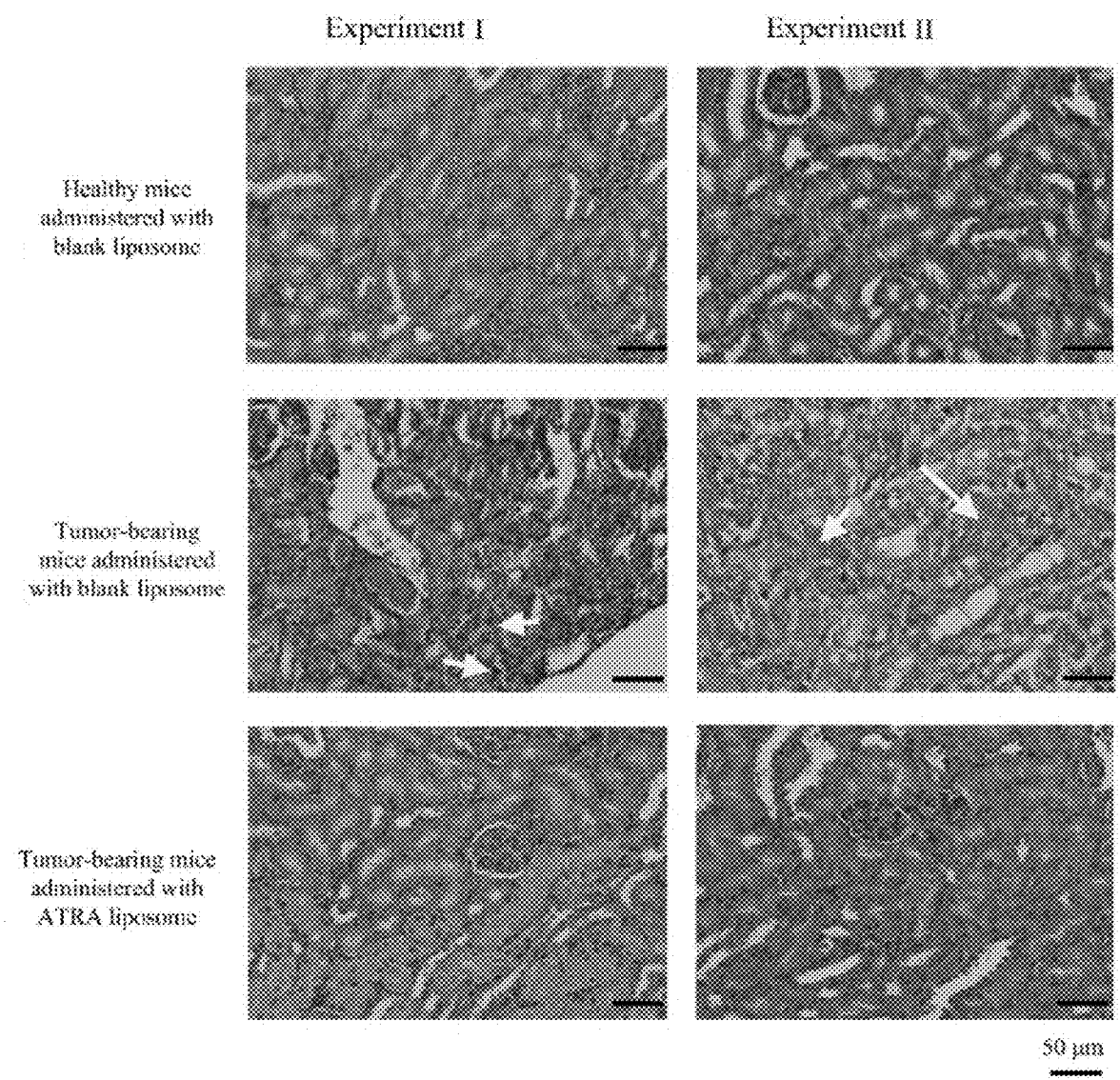
FIG. 12: All-trans retinoic acid injectable formulation reduces kidney tissue invasion and metastasis of tumor cells in 4T1 tumor-bearing mice (white arrows indicate tumor cell invaded lesions).

As a result, as shown in FIG. 11 and FIG. 12, the all-trans retinoic acid injectable formulation prepared in embodiment 3 of the present disclosure can effectively inhibit infiltration and metastasis of tumor cells in the liver of the mouse compared with the mouse liver tissues of the control group (FIG. 11). Meanwhile it can effectively inhibit infiltration and metastasis of tumor cells in the kidney compared with the mouse kidney tissues of the control group (FIG. 12).

The same experimental conclusions are also obtained with respect to each of the all-trans retinoic acid injectable formulation prepared in embodiments 1 and 2. In the 4T1 tumor-bearing mice injected with the all-trans retinoic acid injectable formulation prepared in embodiments 1 and 2, infiltration and metastasis of tumor cells in the liver are less compared with the mouse liver tissues of the control group, and infiltration and metastasis of tumor cells in the kidney are less compared with the mouse kidney tissues of the control group.

The above is only preferred embodiments of the present disclosure and is not any formal and substantial limitations to the present disclosure. It should be noted that a number of modifications and additions may be made by those skilled in the art without departing from the method of the present disclosure, and such improvements and additions are also considered to be within the scope of the present disclosure. Equivalent changes in the variations, modifications, and evolutions that may be made by the above-disclosed technical aspects by anyone skilled in the art, without departing from the spirit and scope of the present disclosure, are all equivalent embodiments of the present disclosure. At the same time, any variations, modifications and evolutions of any equivalent changes made to the above-described embodiments in accordance with the essential art of the present disclosure are still within the scope of the technical solutions of the present disclosure.

What is claimed is:

1. An all-trans retinoic acid injectable formulation, comprising all-trans retinoic acid and solubilizer wherein the solubilizer is consisting of phospholipid, cholesterol and pegylated phospholipid, wherein the phospholipid is selected from any one or a combination more than one of the group of EPC, HSPC and DPPC; and wherein a mass ratio of the lipid to the all-trans retinoic acid is (20-80):1.

2. The all-trans retinoic acid injectable formulation as in claim 1, wherein the pegylated phospholipid is DSPE-PEG2000.

3. The all-trans retinoic acid injectable formulation as in claim 1, wherein the all-trans retinoic acid injectable formulation is a solution, a suspension, an emulsion, or a sterile powder for injection.

4. The all-trans retinoic acid injectable formulation as in claim 1, wherein a concentration of the all-trans retinoic acid is greater than or equal to 0.1 mg/mL.

5. The all-trans retinoic acid injectable formulation as in claim 1, wherein an administration route of the all-trans retinoic acid injectable formulation is selected from the group consisting of intradermal injection, subcutaneous injection, intramuscular injection, and intravenous injection.

6. A pharmaceutical product for treating tumor comprising the all-trans retinoic acid injectable formulation according to claim 1.

7. The pharmaceutical product as in claim 6 for reducing activity of abnormal myeloid-derived suppressor cells, induce differentiation of myeloid-derived suppressor cells, inhibit tumor proliferation and recurrence in cancer patients.

8. The pharmaceutical product as in claim 7, wherein the myeloid-derived suppressor cells are myeloid-derived suppressor cells in patients with breast cancer, colon cancer, ovarian cancer, lung cancer, kidney cancer, stomach cancer, liver cancer, cervical cancer, endometrial cancer, bladder cancer, prostate cancer, pancreatic cancer, colorectal cancer, basal cell carcinoma, melanoma, follicular lymphoma or small lymphocytoma.

9. The pharmaceutical product as in claim 6 has the following effects:
  (1) decreasing a number of myeloid-derived suppressor cells (MDSCs) in tumor infiltrating cells;
  (2) inducing differentiation of tumor infiltrating $CD33^+$ $HLA-DR^-$ cells;
  (3) promoting phenotypic changes of $CD33^+$ cells in peripheral blood mononuclear cells (PBMCs) of cancer patients;
  (4) decreasing inhibition of T cells by $CD33^+HLA-DR^-$ cells in peripheral blood mononuclear cells (PBMCs);
  (5) inducing apoptosis of tumor cells;
  (6) increasing a proportion of infiltrating lymphocytes in tumor tissue;
  (7) inhibiting tumor cell metastasis; and
  (8) delaying tumor growth.

* * * * *